United States Patent [19]
Turner et al.

[11] Patent Number: 5,249,585
[45] Date of Patent: * Oct. 5, 1993

[54] URETHRAL INSERTED APPLICATOR FOR PROSTATE HYPERTHERMIA

[75] Inventors: Paul F. Turner; Theron N. Schaefermeyer, both of North Salt Lake; Amer M. Tumeh, Salt Lake City, all of Utah

[73] Assignee: BSD Medical Corporation, Salt Lake City, Utah

[*] Notice: The portion of the term of this patent subsequent to Nov. 6, 2007 has been disclaimed.

[21] Appl. No.: 609,373

[22] Filed: Nov. 5, 1990

Related U.S. Application Data

[63] Continuation-in-part of Ser. No. 225,307, Jul. 28, 1988, Pat. No. 4,967,765.

[51] Int. Cl.⁵ ............................................. A61N 5/02
[52] U.S. Cl. ................................ 607/99; 128/736; 607/113; 607/116; 607/156
[58] Field of Search ................. 128/804, 784-786, 128/736, 401

[56] References Cited

U.S. PATENT DOCUMENTS

| | | | |
|---|---|---|---|
| 4,154,246 | 5/1979 | LeVeen | 128/784 |
| 4,311,154 | 1/1982 | Sterzer et al. | 128/804 |
| 4,448,198 | 5/1984 | Turner | 128/422 |
| 4,524,550 | 7/1985 | Ruggera et al. | 128/1.5 |
| 4,583,556 | 4/1986 | Hines et al. | 128/804 |
| 4,601,296 | 7/1986 | Yerushalmi | 128/804 |
| 4,658,836 | 4/1987 | Turner | 128/804 |
| 4,669,475 | 6/1987 | Turner | 128/399 |
| 4,676,258 | 6/1987 | Inokuchi et al. | 128/804 |
| 4,681,122 | 7/1987 | Winters et al. | 128/736 |
| 4,700,716 | 10/1987 | Kasevich et al. | 128/804 |
| 4,712,559 | 12/1987 | Turner | 128/422 |
| 4,813,429 | 3/1989 | Eshel et al. | 128/736 |
| 4,860,752 | 8/1989 | Turner | 128/422 |
| 4,967,765 | 11/1990 | Turner et al. | 128/785 |
| 5,003,991 | 4/1991 | Takayama et al. | 128/784 |
| 5,007,437 | 4/1991 | Sterzer | 128/786 |
| 5,057,106 | 10/1991 | Kasevich et al. | 128/804 X |

FOREIGN PATENT DOCUMENTS

| | | | |
|---|---|---|---|
| 03760890 | 5/1990 | European Pat. Off. | 128/804 |
| 3534124 | 2/1987 | Fed. Rep. of Germany . | |
| 8103616 | 12/1981 | PCT Int'l Appl. | 128/804 |

OTHER PUBLICATIONS

Andrew Wu, et al., "Performance Characteristics of a Helical Microwave Interstitial Antenna for Local Hyperthermia", Mar./Apr. 1987, Med. Phys, 14(2), pp. 235–237.

(List continued on next page.)

*Primary Examiner*—Lee S. Cohen
*Attorney, Agent, or Firm*—Mallinckrodt & Mallinckrodt

[57] ABSTRACT

A urethral inserted applicator for prostate hyperthermia includes a multi-tube, balloon type catheter. The catheter includes first and second closed end fluid dry tubes, respectively, for a helical coil electrode type applicator, and an electromagnetic field compatible temperature sensor for measuring the temperature of the prostate tissue, and an open fluid receiving tube enabling urine drainage from the bladder. A radiofrequency source supplies electromagnetic energy to the applicator. A control unit contains a comparator which is connected to the temperature sensor and a temperature reference device for comparing the actual tissue temperature level with a desired temperature level and output control signals to the radiofrequency generator for controlling the output to the applicator. The coil type applicator is an elongated coil connected to the center conductor of a coaxial cable. A second electrode is connected to the outer conductor of the connecting cable providing a ground current return of the heating current. A sheet or sheath of insulation material covers the coil electrode for insulating the coil from the tissue and the thickness of the sheet may be varied to provide uniform tissue heating along the length of the coil. The balloon of the catheter engages the body's bladder to position the applicator properly during the treatment.

20 Claims, 9 Drawing Sheets

OTHER PUBLICATIONS

El-Deek M. El-Sayed et al., "Use of Sheath Helix Slow-Wave Structure as an Applicator in Microwave Heating Systems" 1981, Journal of Microwave Power, 16 (3 and 4), pp. 283-288.

Jozef Mendecki et al., "Microwave Applicators for Localized Hyperthermia Treatment of Cancer of the Prostate", Nov. 1980, Int. J. Radiation Biol. Phys., vol. 6, No. 11, pp. 1583-1588.

Tadashi Harada, et al., "Microwave Surgical Treatment of Diseases of Prostate", Urology, Dec. 1985 vol. XXVI No. 6, pp. 572-576.

Ding-Jiu Li, et al. "Design & Thermometry of an Intracavitary Microwave Applicator Suitable for Treatment of Some Vaginal & Rectal Cancers", Nov. 1984 Int. J. Radiation Oncology Biol. Phys. vol. 10, pp. 2155-2162.

Leonid Leybovich, et al., "Intracavitary Hyperthermia: A Newly Designed Applicator for Tracheal Tumors:", Jan. 1987, Endocurietherapy/Hyperthermia Oncology, vol. 3, pp. 23-29.

Toru Satoh, et al., "Thermal Distribution Studies of Helical Coil Microwave Antennas for Interstitial Hyperthermia", Int. J. Radiation Oncology Biol. Phys. vol. 15, pp. 1209-1218.

P. B. Dunscombe et al., "Heat Production in Microwave-Irradiated Thermocouples", Med. Phys. 13 (4), Jul./Aug. 1986.

R. T. Constable et al., "Perturbation of the Temperature Distribution in Microwave Irradiated Tissue Due to the Presence of Metallic Thermometers", Med. Phys. 14 (3), May/Jun. 1987.

Leonard S. Taylor, "Electromagnetic Syringe" IEEE Transactions on Biomedical Eng., vol. BME-25, No. 3, May 1978.

Medical Tribune, vol. 29, No. 9, Thursday, Mar. 31, 1988, "Transurethral Hyperthermia for BPH: Trial's Goal is to Top 80% Success", by Rick McClure, pp. 3, 13, 14.

M. A. Astrahan, et al., "Microwave Applicator for Transurethral Hyperthermia of Benign Prostate Hyperplasia" May/Jun. 1989, International Journal of Hyperthermia, vol. 5, No. 3, pp. 283-296.

URETHRAL INSERTED APPLICATOR FOR PROSTATE HYPERTHERMIA

RELATED APPLICATIONS

This application is a continuation-in-part of copending application Ser. No. 07/225,307 filed Jul. 28, 1988, now U.S. Pat. No. 4,967,765.

BACKGROUND OF THE INVENTION

1. Field

This invention relates to electromagnetic radiation antenna or electrode devices for medical hyperthermic purposes, and more particularly to a combined catheter and applicator for treating prostatomegaly such as benign prostatic hypertrophy, prostatitis, and prostate malignancy by urethral insertion.

2. State of the Art

Hyperthermia or induced high body temperature has been considered beneficial in treating various human diseases including many types of cancer. More specifically, various types of malignant growths are considered by many researchers to have a relatively narrow hyperthermia treatment temperature range. Below a threshold temperature of about 41.5 degrees Celsius, thermal destruction of these malignancies is not possible, and, in fact, their growth may be stimulated. However, at temperatures above a range of about 43 to 45 degrees Celsius thermal damage to most normal body tissue cells occurs if exposure lasts for even a relatively short duration.

While some types of skin cancers are known to respond to direct application of surface heat, deeply located malignant growths, owing to normal blood flow body heat transfer properties of the body, were most difficult to heat to the desired temperature without damaging overlying healthy tissue. A solution to this problem has been the development of electromagnetic radiation (EM) heating devices for inducing hyperthermia. This form of treatment is known as "diathermia".

EM heating of subsurface growths from an exterior surface is ordinarily enabled by configuration and placement of one or more applicators and by appropriate selection EM frequency, phase and intensity. Nevertheless, tissue growths inside of, or in close proximity to, heat sensitive tissue or organs, are much more effectively and safely heated by EM irradiating applicators positioned within the body as closely as possible to the growth requiring treatment.

The advantages of positioning EM applicators relatively close to the growth to be heated by radiation include improved heating control, more localized heating and consequently less possibility of overheating adjacent healthy tissue and more direct treatment of the enlarged tissues causing the undesirable symptons.

Close applicator access to certain types of diseased tissue growths is provided by surgical procedures for naturally occurring body passages such as the esophagus, larynx, prostate gland and colon. Surgical procedures enlarge the passage by cutting away the passage tissue. Some heating methods use small EM applicators placed over the tissue or in an incision to provide direct irradiation of the growth. An illustrative type of a body passage insertable EM applicator is described in U.S. Pat. No. 2,407,690 issued to Southworth. The Southworth type body passage EM applicators have been configured to cause a heating pattern that tends to be concentrated at the radiating tip of the applicator and which decreases at a usually exponential rate from such tip toward the radiation source.

Special and difficult problems often attend growths found along natural body passages. For example, diseased tissue tends to spread around and along the passage, often in a relatively thin layer. Typically, the diseased layer may be less than a centimeter thick and may extend as far as 6–10 centimeters along the passage. The use of Southworth type applicators result in nonuniform irradiation heating of the elongated growth. Thus, the temperature at the tip of the Southworth type applicator may have to be so hot that it kills surrounding healthy tissue in order to make the portion of the applicator toward the power supply hot enough to kill the growth.

Ridged and non-flexible antenna rectal-inserted devices are known. Examples of such devices are disclosed in U.S. Pat. No. 4,601,296 issued to Yerushalmi, and a 1980 article titled "Microwave Applicators for Localized Hyperthermia Treatment of Cancer of the Prostate" by Mendecki et al., Int. J. Radiation Oncology, Biol. Phys., Vol. 6, pp. 1583 and 1588.

Also helical coil designs have been used to heat tissue placed within the cylindrical opening of the device. Such devices are disclosed in U.S. Pat. No. 4,527,550 issued July 1985 to Ruggera.

A body passage insertable applicator apparatus for EM systems is known that includes a urethral inserted probe having a monopole antenna (Microwave Surgical Treatment of Diseases of Prostate, Harada et al., Urology, December 1985, Vol. XXVI, No. 6, pp. 572–576). This device of Harada has no position fixing device to reliably provide correct placement. It also does not include a temperature monitoring device to monitor the prostate tissue or a means of controlling the treated prostate tissue at a preset target temperature. The Harada device does not include a fluid drainage device to enable urine drainage for prolonged treatment. The Harada device is described as more of a microwave surgery device which applies a large amount of power to a short length of tissue for a short time to cause lethal damage to the tissue. If a longer length of tissue along the urethra is to be treated, multiple treatments of short, adjacent lengths of tissue are required, with the antenna manually repositioned along the urethra between each treatment. Tissue temperatures far above 50° C. are intended in treated tissue to cause tissue coagulation of the treated tissue. This high uncontrolled temperature is noted by Harada to have caused "destruction of the prostate itself" in animal experiments. "On histologic examination, an extensive necrotic region with hemorrhage was noted immediately after the procedure." Although the Harada device and procedure appeared to provide some benefit to some patients, the uncontrolled procedure and system presents undesirable possible risk to the patients. The difficulty in positioning, controlling, and the general use of the Harada devices appear not very practical since the suggested normal positioning is by "rectal examination or trans-abdominal echography".

Also known is a helical wound coil applicator having coaxial inner and outer conductors electrically connected at an EM input end to a conventional coaxial transmission line for transmitting high frequency EM from a source to the applicator. The applicator outer conductor is longitudinally split on opposite sides to form first and second outer conductor segments. The inner conductor is electrically connected to an applicator termination end of one of such segments. A dielectric media is disposed between the applicator inner and outer conductors, and the outer conductor and termination end are covered by a dielectric sheath. A substantially uniform, external electric tissue heating field is obtained along substantially the entire length of the applicator by exponentially increasing the thickness of the dielectric sheath over the termination end and making the thickness of the sheath over the termination end equal to at least half the outer diameter of the applicator. Those persons skilled in the art desiring further information concerning this device are referred to U.S. Pat. No. 4,658,836 issued Apr. 21, 1987 to Paul F. Turner.

A principal feature distinguishing the present invention from the prior art devices in the provision of a urethral insertable EM applicator principally adapted for benign prostatic hyperplasia (BPH), which provides the generally cylindrical or longitudinally uniform EM heating pattern necessary to enable substantially uniform heating of BPH growths or other tissue diseases associated with the urinary track.

SUMMARY OF THE INVENTION

Accordingly, it is an object of the invention to provide an improved treatment of benign prostatic hyperplasia as well as other diseases of the prostate gland locally involved around the urethra.

Another object of the invention is to provide an EM applicator apparatus meeting the clinical requirements of high flexibility, sterilization, disposability, low cost, urinary drainage, and integral temperature monitoring along the perimeter of the urethral wall. The integral inflatable balloon section provides an automatic positioning of the applicator heating zone within the prostate tissue area. This section is intimately attached to the bladder enlarged neck opening. In this way, the applicator can be secured in place and will remain properly positioned during the treatment even though size and length of the urethral passage may change over the extended treatment period.

Yet another object of the invention is to provide an urethral insertable radiofrequency EM applicator which provides the generally cylindrical or longitudinally uniform EM heating pattern necessary to enable substantially uniform heating of BPH growths or other tissue diseases associated with the urinary tract.

A further object of the invention is to provide an urethral insertable EM applicator which can be positioned with respect to the prostate and maintained against movement therefrom during treatment.

Briefly stated, the urethral insertable radiofrequency EM applicator system includes a controlled source of EM connected to an electrical coiled conductor housed in a catheter. A temperature controller includes a sensor for determining the temperature of the surrounding tissue and generating control signals for the source of EM.

The catheter includes an applicator positioning means for automatically positioning the coiled conductor adjacent the prostate gland and for maintaining the position during the treatment. The electrical coil is suitably sheathed to provide an external, substantially uniform, electric tissue heating field to be radiated at nearly all transverse cross sections along the applicator for substantially uniform tissue heating.

Advantages of the present invention are the provision of a low cost, disposable applicator which is detachably connected to a modified balloon type catheter for the treatment of BPH. BPH is usually treated by surgery with significant side effects. These side effects include hemorrhage, impotency, anesthetic complications, and technical failures. The use of the combined applicator catheter apparatus involves a treatment which requires no anesthesia or surgery and requires only 1 or 2 hour office visits to accomplish in comparison to post surgical hospitalization.

BRIEF DESCRIPTION OF THE DRAWINGS

Other objects and features of the invention will become more readily apparent from the following detailed description when read in conjunction with the accompanying drawings, in which.

DETAILED DESCRIPTION OF A PREFERRED EMBODIMENT

Figure 1:
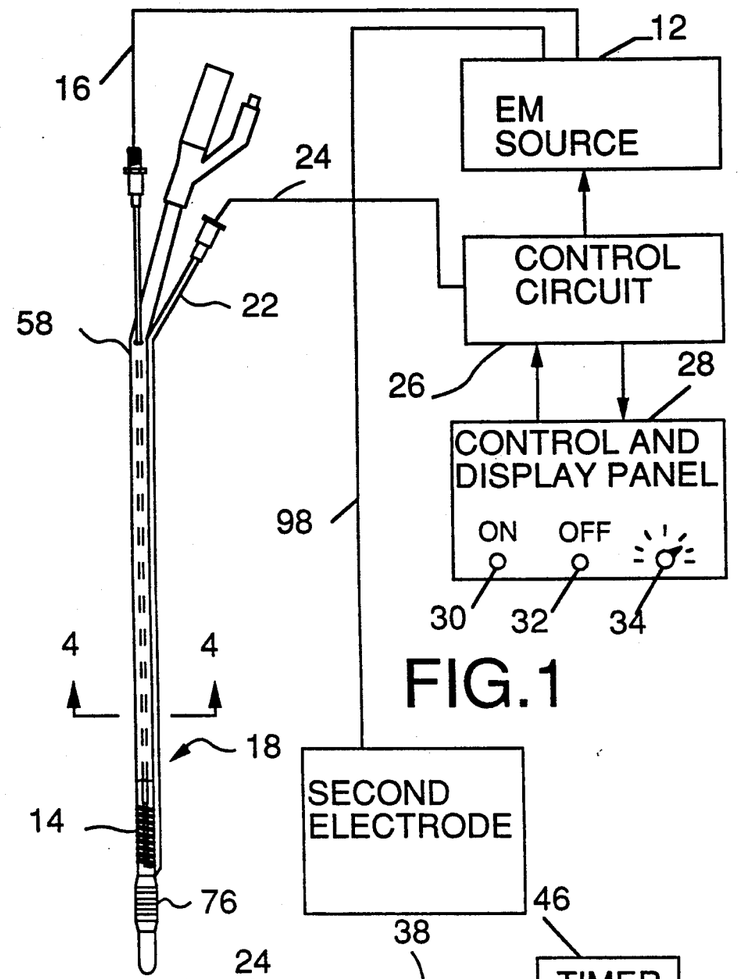
FIG. 1 is a view of the urethral insertable radiofrequency EM capacitive electrode applicator system showing the schematic diagram in block form.

Referring now to FIG. 1, the urethral insertable radiofrequency electromagnetic (EM) capacitive applicator system includes an electromagnetic energy source 12 having an oscillator for supplying a maximum of about 40 watts electrical power at a frequency of between 100 kHz to 300 MHz (typically 13, 27, or 40 MHz would be used since they are approved by the FCC for medical use), for example, to an electromagnetic electrode 14 through a connector means in the form of a connector cable 16 extending through a catheter 18 from electrode 14 to outside the catheter and a coaxial cable 17 connected to the end of connector cable 16. A suitable cable for both the connector cable 16 and coaxial cable 17 is a typical RG-178B cable or one of equivalent size. The cables 16 and 17 could also be of other common types such as two twisted wires or even a single wire connected to the tip of electrode 14. The electrode 14 is an emitter of electromagnetic energy with such energy emitted from a flexible metallic surface such as a metal wire braid, a flexible conductive rubber sleeve, several wire strips, several metal sleeves or a helical coil mounted in a catheter 18 with the electrode soldered or electrically attached by direct contact to the tip of the electrically active conductor of connector cable 16, such as the inner conductor of a coaxial cable. The catheter 18 is, for example, a size twelve French catheter modified as hereinafter described. With the particular applicators and radiofrequency EM energy described, a second electrode is needed to provide a current return path to EM source 12. Heating current flows from source 12 through cable 17 and connector cable 16 to applicator 14. The current flows from applicator 14, through the tissue to be heated, to second electrode 96 and then back through cable 98 to source 12. Current flow between applicator 14 and second electrode 96 is due to the capacitance between the two. The second metallic electrode 96 can either be contacting the patient or be separated by a dielectric media such as plastic, rubber, or air. For example, the second electrode can be inserted into the rectal passage to a position therein adjacent the prostate gland, can be placed against the skin surface in the pelvic region, or can be displaced away from the skin in the pelvic region. While second electrode 96 is shown as a single electrode, it could take the form of several electrodes. Further, the second electrode 96 could be in the form of a table or other supporting surface for the patient during treatment, and the return path indicated by cable 98 may merely be through the ground plane connections. In any situation, the metallic surface area of the second electrode 96 should be larger than that of the primary heating electrode applicator 14 placed within the prostate gland. In some cases, particularly where higher frequencies are used, the outer braided conductor of connector cable 16 can act as the second electrode. In such case, current would flow from applicator 14 through the adjacent tissue back along connector cable 16 and capacitively couple to the outer, return conductor which provides the return path to EM source 12.

The inserted radiofrequency EM applicator electrode 14 may be in the form of one of the following:
a) a helically wound metal coil;
b) multiple wrapped coils co-located at the same zone;
c) a cylindrical sleeve made of multiple over lapping wires or a metallic cylinder;
d) multiple electrodes or coils stacked longitudinally and connected to individual transmission lines, wires, or coaxial cables to allow modification of the heat pattern length using either coherent or non-coherent phase energy into each coil;
e) straight but flexible electrode conductors rather than coiled conductors;
f) a coil with non-uniform conductor width or turns density along the coil length to modify the capacitive coupled current distribution from uniform to modify the heating distribution along the length; and
g) an electrode or coil with dielectric material around the electrode or coil, but with the dielectric material modified or the thickness of the dielectric material varied around the electrode or coil to modify the heating distribution along the length of the electrode or coil.

Figure 2:
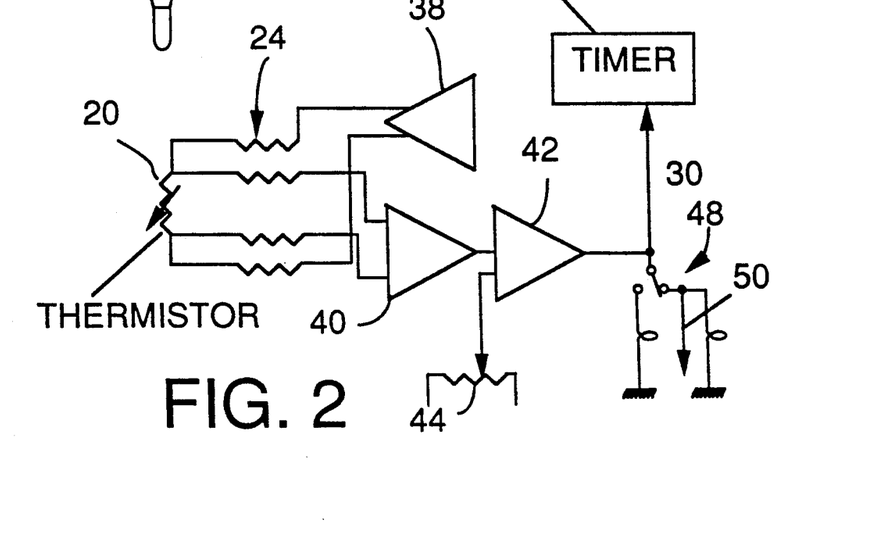
FIG. 2 is a functional schematic view of the temperature sensor and radiofrequency EM source control functional circuits.

A separable insulated temperature sensor 20, shown by electrical schematic in FIG. 2, is inserted in a flexible tube 22, FIG. 1, during treatment. The tube is attached exteriorly of the catheter 18 adjacent to the antenna 14. The temperature sensor measures the temperature of the tissue surrounding the catheter. The temperature sensor is connected by an insulated four resistive lead cable 24 to a temperature sensor circuit and electromagnetic power source control circuit 26. The EM power source control circuit has its output connected to the EM energy source 12 for maintaining a power supply sufficient to maintain a tissue temperature between about 41.5 degree Celsius up to 50 degree Celsius. A control and display panel 28 is connected to the temperature sensor circuit and EM control circuit 26 for two way communication. The control and display panel 28 includes EM energy on/off switch buttons 30 and 32, and a temperature controller 34 for setting the desired operating temperature for the temperature sensor circuit and EM power control.

The temperature sensor circuit and EM control circuit 26, FIG. 1, includes the temperature sensor 20, FIG. 2, which may be a typical precalibrated thermistor sensor connected to a constant current source 38. An amplifier 40 is connected to the thermistor 20 for amplifying the thermistor output to a working level. A high gain comparator 42 has input terminals connected to the amplifier 40 and to a temperature setting potentiometer 44 of the temperature controller 34 located on the control and display panel 28, FIG. 1, for comparing the amplified thermistor output with a desired temperature reference voltage and outputting switch control signals. The high gain comparator 42, FIG. 2, has its output connected to the junction of a timer 46 and an electrically controlled pole of a double pole switch 48. A secondary temperature sensor 20, lead 24, and control circuit 26 can be added for a redundant monitor. This could be inserted into other tissue or in a second flexible tube 22.

The timer 46 is the EM power source control. The timer is triggered in response to the initial receipt of power from the comparator 42 for measuring a preselected treatment time, and at the end of the timing period cuts off the EM power source. In addition, the pole of the switch 48 is manually controlled by the switch control on/off buttons 30 and 32. When the switch is positioned on, as shown, a control signal is output on lead 50 to power on the EM power source; conversely when the switch 48 is turned to the Off position, the EM power source is turned off. It should be noted the timer 46, comparator 42, temperature setting potentiometer 44, control switch 48, and portions of the control circuit can be replaced by a small computer chip operating in an equivalent manner.

Figure 3:
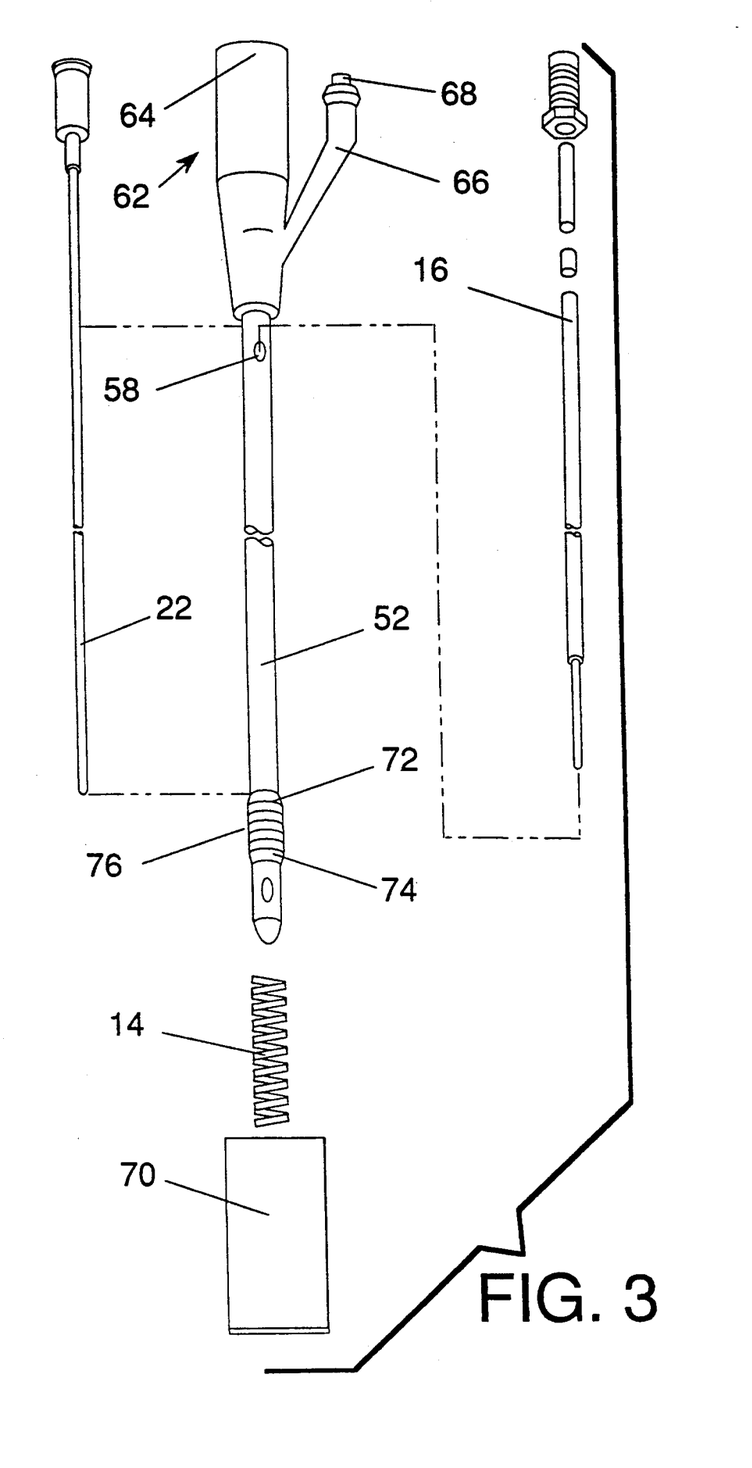
FIG. 3 is an exploded view of the urethral insertable EM applicator.
Figure 4:
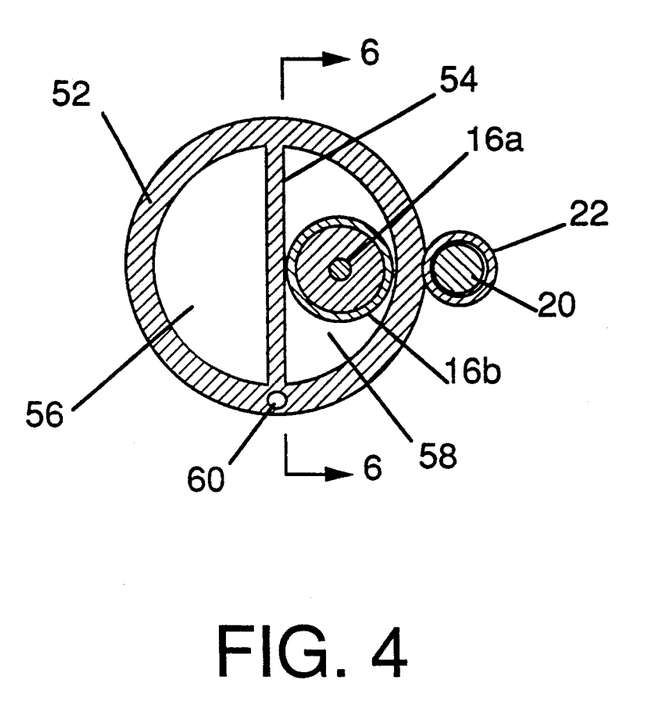
FIG. 4 is a transverse section of the urethral insertable EM applicator taken as to line 4—4 of FIG. 3.

The catheter 18 of the combined catheter and applicator is, for example, a balloon type urological catheter having a flexible, plastic tubular body 52, FIGS. 3 and 4, which is divided by a partition 54, FIG. 4, into a catheter drainage tube 56, a fluid isolated tube 58, and a fluid passage 60 for inflating balloon 76. The flexible tube 22 for the temperture sensor is attached exteriorly of the tubular body 52. The tubular body 52 has a bifurcated opening piece 62 having one side 64 for connecting the central drainage tube 56 to a waste receiving receptacle, and a second side 66 having an air or fluid input/output valve 68 for connecting the air or fluid passage 60 to a pressurized air or fluid supply source to inflate the balloon 76 after insertion into the bladder. This air or fluid supply source could simply be a syringe.

In operation, with the catheter properly positioned as described above, and the timer 46 and the temperature set dial set as desired, the EM oscillator 12 is turned on by RF switch 30 and the applicator 14 radiates power into the area of the prostate gland until the desired temperature is reached. When the desired temperature is reached, the comparator 42 outputs control signals to the oscillator to manipulate its EM output power to maintain the temperature substantially constant for the selected treatment time period. At the end of the treatment time, the oscillator is automatically turned off, but the oscillator can be turned off at any time using the EM off switch 32.

The transmission line, wire or coaxial cable forming connector cable 16, FIG. 3, passes through the fluid isolated tube 58 through outlets adjacent ends of the electrode or antenna forming coil to connect to the electrode or antenna coil 14 as previously described. A dielectric sheet 70 or tube, such as, for example, a silicone rubber, is placed and bonded over the metal electrode or spiral metal coil 14 to complete the applicator. The sheath 70 is the means for causing the external, electric tissue heating field to be substantially uniform along the length of the applicator and avoiding direct metallic contact between the metal portions of the electrode or antenna. It may be allowable for such metal surfaces to contact the tissues directly if sufficient protection is provided to assure that potentially dangerous currents at dc or frequencies below 100 kHz cannot flow into the tissues. Such low frequencies can improperly stimulate muscle spasms, cramping, and damage. The thickness of the preferred dielectric sheath may be uniform or may be varied exponentially, if necessary, to obtain the uniform heating field. The electrode or antenna coil 14 is positioned adjacent to the edge 72 of the inflatable balloon 76 toward the proximal end of the catheter.

FIG. 4 shows the cross-section view 4—4 from FIG. 1 of the body of the Foley catheter applicator assembly 18. The Foley balloon is in open communication with the outlet of the air or fluid passage 60 which enables inflation and deflation of the balloon section. Thus, when the catheter is positioned so that the balloon when inflated is in the bladder, and then the catheter is pulled outwardly so that the inflated balloon is resting on the neck of the bladder, the applicator is properly positioned with respect to the prostate gland and will maintain its position free from movement for the duration of the hyperthermic treatment. FIG. 4 shows the urine drainage passage 56 and the fluid dry passage 58 through which the connector cable 16 passes. The connector cable is preferably comprised of an outer conductor 16b and an inner conductor 16a separated by a dielectric 16c. At least one externally attached temperature probe receiving tube 22 is attached to the Foley catheter outer wall 52 enabling insertion of a temperature sensor 20.

Figure 5:
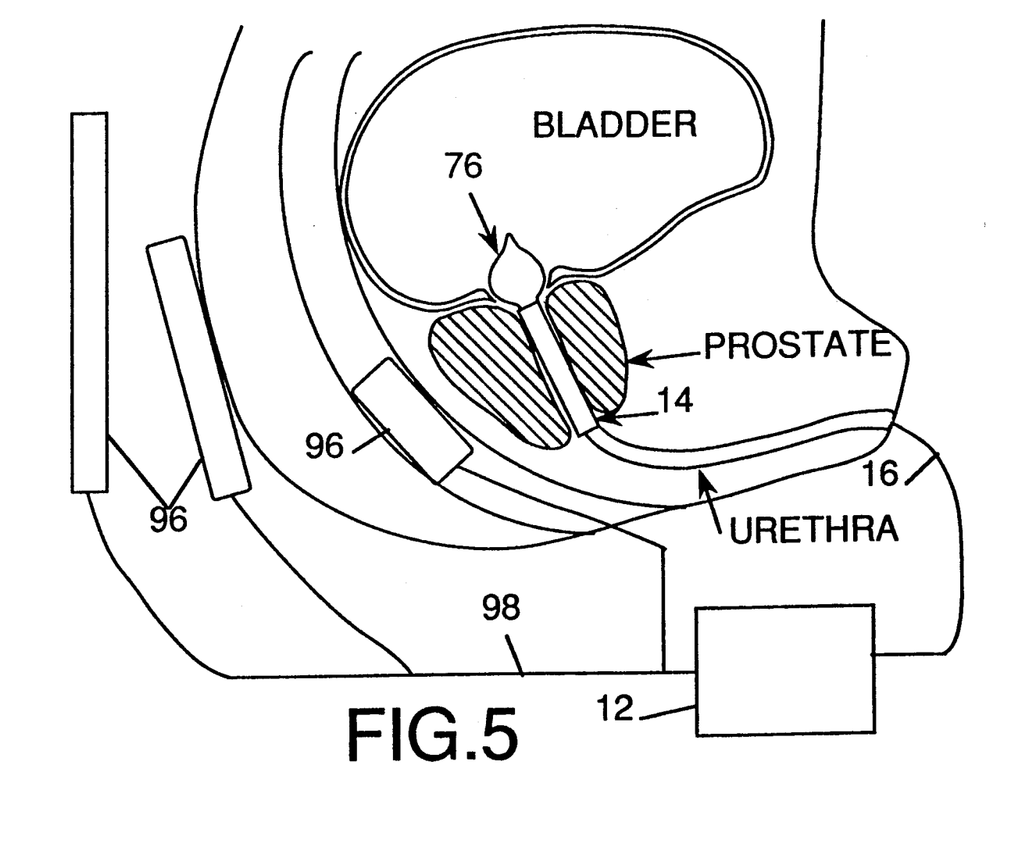
FIG. 5 is a vertical section of the pelvic region of a human male body showing the positioning of the electrode applicator in treatment position within the prostate gland and the balloon in the bladder neck.

FIG. 5 is a cross-sectional representation of the insertion of the urethral inserted applicator electrode 14 in the urethra in the prostate gland. The coil style electrode 14 is represented as being positioned in the prostate because the balloon 76 has been inflated and secured against the bladder wall at the neck of the bladder opening into the urethra. Also, the second electrode 96 is represented with three alternate configurations, all shown in FIG. 5. In one position, the second electrode 96 can be inserted into the rectal passage 97 and positioned approximately adjacent to the prostate gland. In a second position, it can be placed along the skin surface in the pelvic region, the position shown merely being an example. In a third position, second electrode 96 can be displaced away from the skin in the pelvic region, again, the position shown in FIG. 5 merely being an example. Any of these second electrode positions can be used to provide a capacitively coupled current return path for the current flowing from electrode 14. The second electrode 96 provides a return current flow path to the EM source 12 via connecting cable 98. The inflated balloon 76 is shown in the proper treatment position against the bladder wall.

Figure 6:
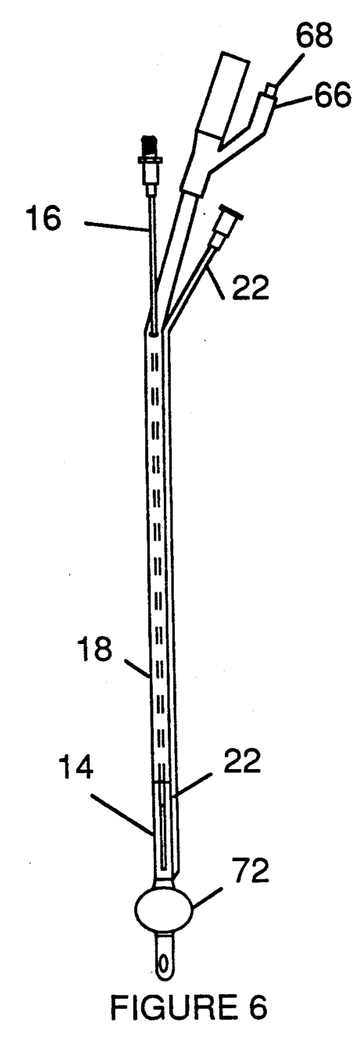
FIG. 6 is an elevational view of a catheter of the invention showing the inflation of the balloon section.

As shown in FIG. 6, the tip balloon 76 can be inflated or filled with water or air to enable securing it into place at the neck of the bladder. The balloon inflation and deflation is provided by the stopper valve 68 which is connected to the applicator body 18 by tube support 66.

Figure 7:
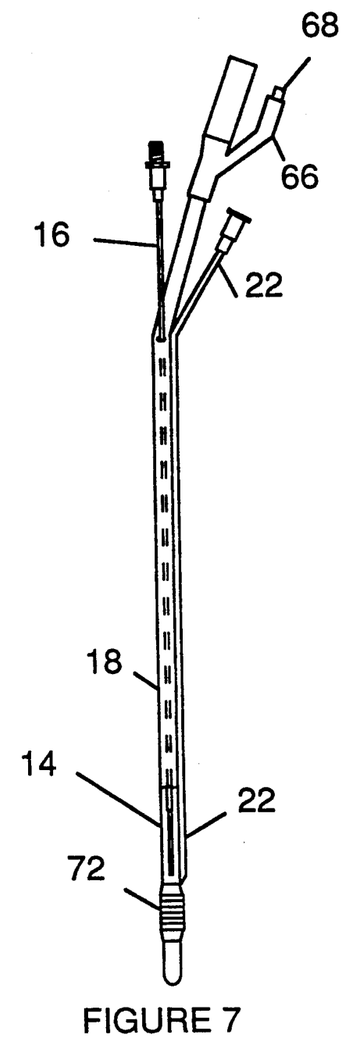
FIG. 7 is a view similar to FIG. 6 without the balloon inflated and showing the basic modified catheter with a non-specific applicator section.

FIG. 7 shows the tip balloon 76 in the deflated mode for the insertion into or removal from the bladder and urethra. The balloon inflation and deflation is provided by the stopper valve 68 which is connected to the applicator body 18 by tube support 66.

Figure 8:
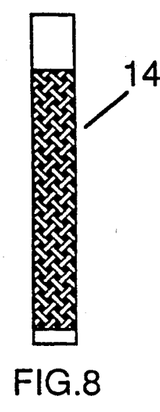
FIG. 8 is a view of a wire braid or shield configuration of the applicator electrode.

FIG. 8 shows the configuration of a flexible conductive electrode applicator 14 comprised of multiple over lapping strands of wire forming an inter-twined braided cylinder.

Figure 9:
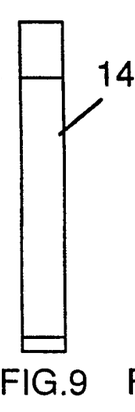
FIG. 9 is a view of a flexible conductive rubber or metallic plating configuration of the applicator electrode.

FIG. 9 shows the applicator 14 as a flexible conductive cylindrical electrode comprised of a conductive rubber or plated dielectric surface. This type of material is commercially available.

Figure 10:
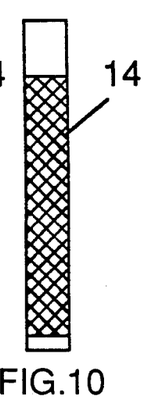
FIG. 10 is a view of a flexible multiple wire coil configuration of the applicator electrode wound in opposing directions.

FIG. 10 shows the applicator 14 as a flexible conductive electrode comprised of several crossing wires in a wrapped braid form where the wires are wound in a coiled or weaved fashion.

Figure 11:
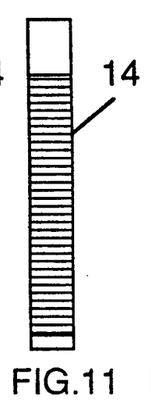
FIG. 11 is a view of a helical coil wire wrap configuration of the applicator electrode.

FIG. 11 shows the applicator 14 as a flexible conductive electrode comprised of a single wire coil being wrapped along the full electrode length.

Figure 12:
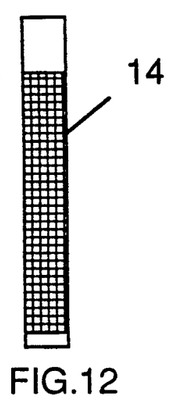
FIG. 12 is a view of a wire mesh or screen configuration of the applicator electrode.

FIG. 12 shows the applicator 14 as a flexible conductive electrode comprised of a wire grid or screen.

Figure 13:
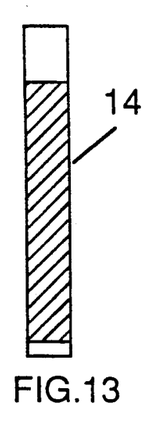
FIG. 13 is a view of a multiple wire coil wrap configuration of the applicator electrode.

FIG. 13 shows the applicator 14 as a flexible conductive electrode comprised of several non-overlapping wires which are wound in parallel coils along the same length section.

Figure 14:
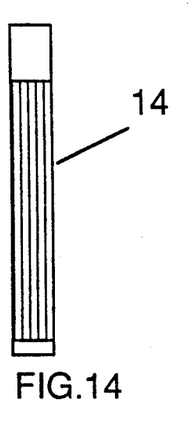
FIG. 14 is a view of a multiple flexible wire configuration of the applicator electrode.

FIG. 14 shows the applicator 14 as a flexible conductive electrode comprised of several parallel wires which run the full length of the flexible electrode. These wires are connected with a common input wire and can be shorted together at the tip region if desired.

Figure 15:
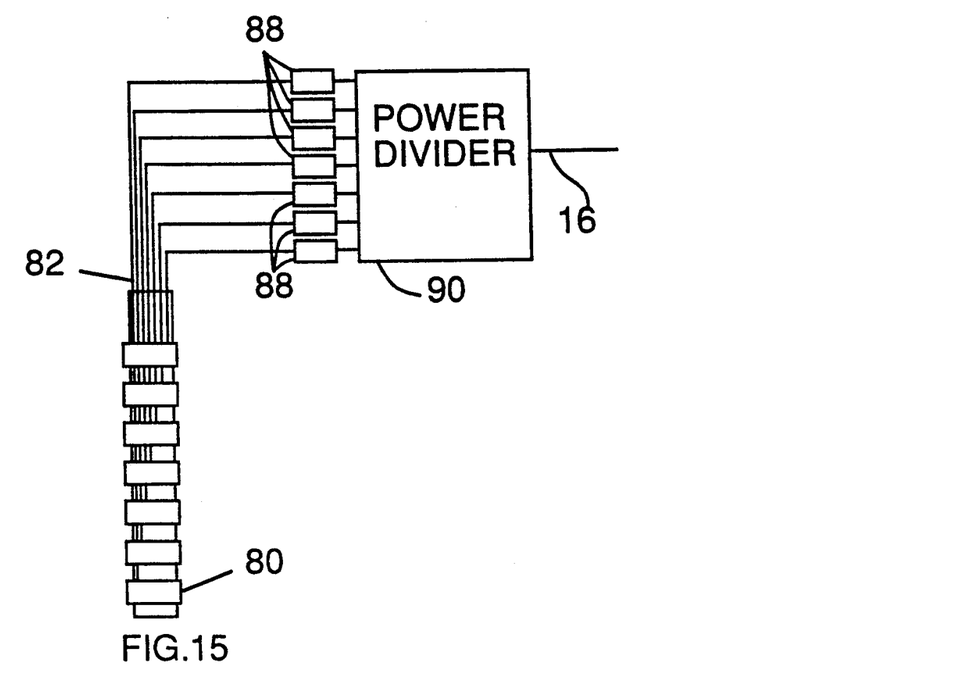
FIG. 15 is a view of longitudinally stacked electrodes connected by independent wires to the controlling electromagnetic generator.

FIG. 15 shows the system connection configuration for applicator 14 when applicator 14 is in the form of a multiple sleeve, flexible, conductive electrode comprised of several conductive collars 80 stacked along the electrode length to enable separate zones of heating which are individually connected with the multiple wires or cables 82 through power control devices 88 and power divider 90 to the EM source connection cable 17. The use of separate wires to separate zones enables the connection to the EM source to be individually interrupted by the power control devices 88 which are power attenuators, amplifiers or switches. In this way, the heating can be diminished along selected portions of the heating length. This would be useful, for example, if the prostate tissue to be treated is not as long as the electrode array. Thus, by simply disconnecting the connection of the wires to the EM source which correspond to the electrodes where the heat is not desired, the heating length can be adapted to match the intended target tissue length. One connection wire 82 is connected to each of the conductive electrodes 80. The power control devices 88 are each connected to the power divider 90 which divides the power received from the EM source connection cable 17.

Figure 16:
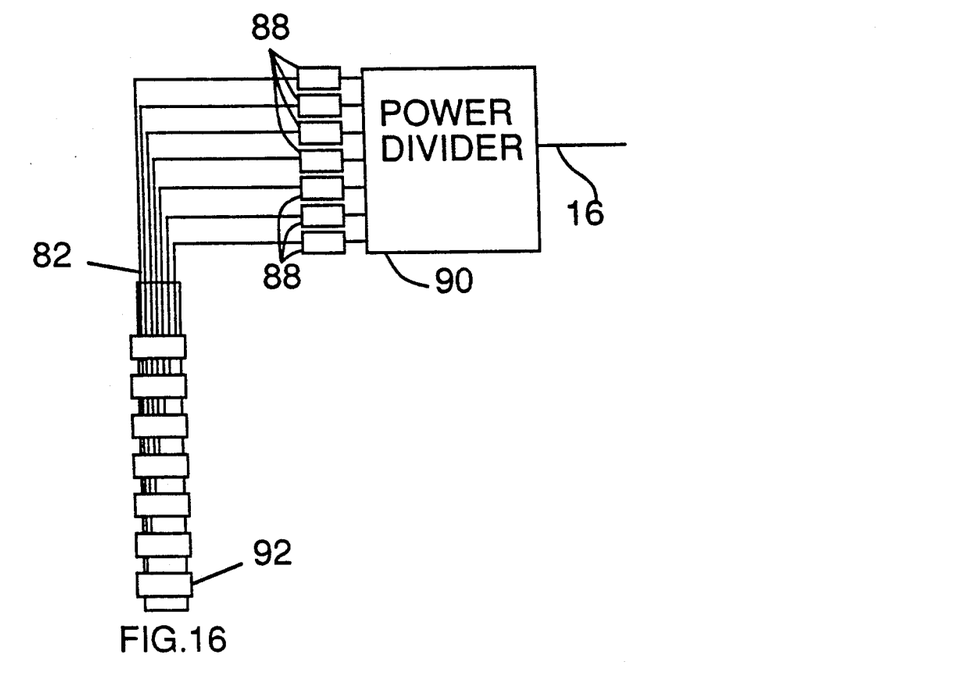
FIG. 16 is a view of longitudinally stacked coil electrodes connected by independent wires to the controlling electromagnetic generator.

FIG. 16 shows the system connection configuration of the applicator 14 when applicator 14 is in the form of multiple coil sections forming a flexible conductive electrode comprised of several conductive collars 92 stacked along the electrode length to enable separate zones of heating which are individually connected with the multiple wires or cables 82 through power control devices 88 and power divider 90 to the EM source connection cable 17. The use of the these wires to separate zones enables the connection to the generator to be individually interrupted by the power control devices 88 which are power attenuators, amplifiers or switches. In this way the heating can be diminished along selected portions of the heating length. This would be useful for example if the prostate tissue to be treated is not as long as the electrode array. Thus, by simply disconnecting the connection of the wires to the generator which correspond to the electrodes where the heat is not desired, the heating length can be adapted to match the intended target tissue length. One connection wire 82 is connected to each of the conductive coils 92.

Figure 17:
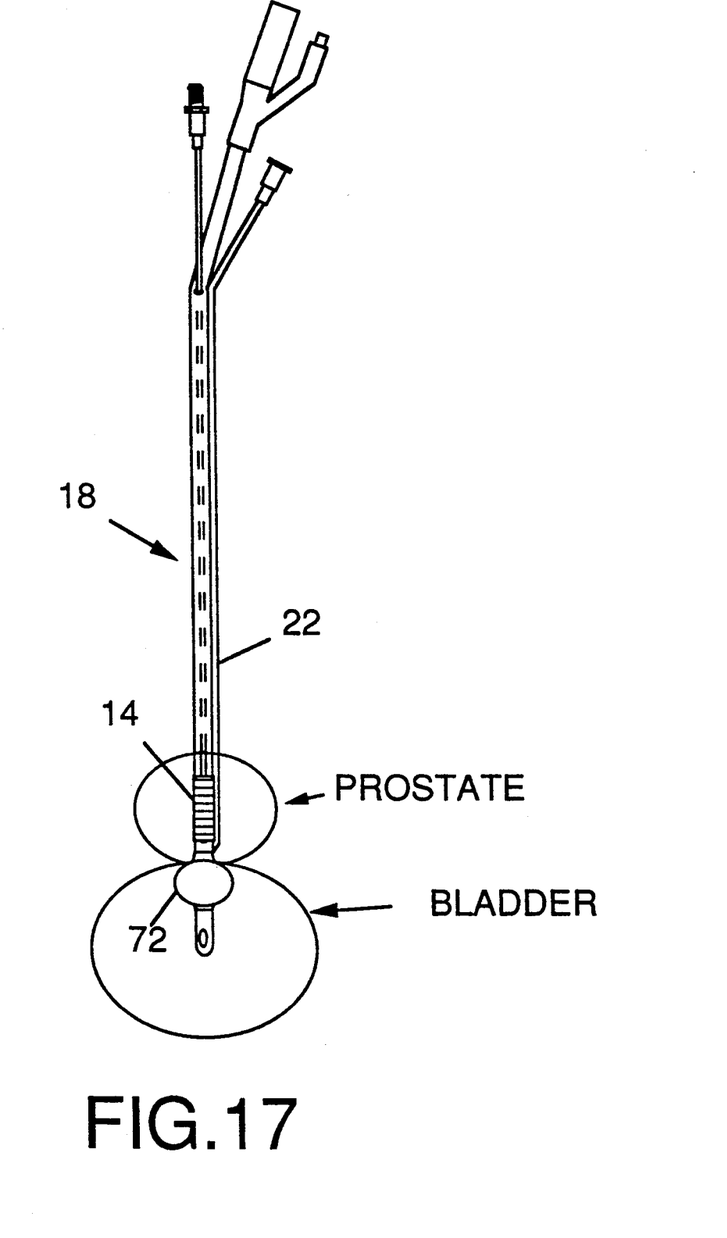
FIG. 17 is a view of an applicator diagrammatically installed in the bladder and prostate to show the treatment positioning of the balloon and applicator.

FIG. 17 shows the orientation of the applicator electrode 14 in the prostate gland and the balloon 72 inflated at the bladder opening. When the balloon is inflated, the Foley catheter assembly 18 can be manually pulled to position and secure the balloon at the bladder neck. This assures that the heating pattern is correctly positioned within the prostate gland which rests next to and attached to the bladder wall.

Figure 18:
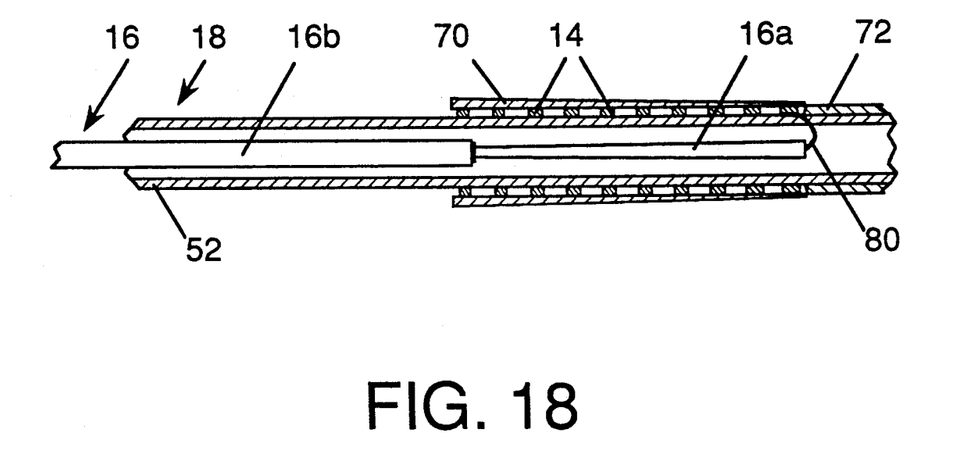
FIG. 18 is a cross-sectional view of a helical coil embodiment of the radiofrequency capacitive electrode applicator.

FIG. 18 shows the cross-sectional view along the line 18—18 of FIG. 4 of the applicator heating electrode or coil section 14. The outer conductor 16b of the EM source connection cable 16 is shown passing within the Foley catheter body wall 52. The center conductor 16a is shown connected to the applicator electrode 14 by connecting wire 80. The coil configuration of electrode 14 can have varying conductor width to modify the heating current distribution as shown. The dielectric sheet layer 70 wrapped around and bonded to the electrode 14 normally is of uniform thickness, but can have varying thickness as shown to modify the coupling distribution of the heating currents passing from the electrode 14 to the tissues through the dielectric capacitance provided by the dielectric layer 70. The balloon 76 is located at the distal end of the inserted electrode 14.

Whereas this invention is here illustrated and described with specific reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

What is claimed is:

1. An electromagnetic capacitive coupling applicator apparatus for treatment of benign prostatic hyperplasia comprising:

catheter means for insertion into the urethra;

applicator means carried by the catheter means, said applicator means including an applicator and a connector means for connecting the applicator to a source of electromagnetic energy, said applicator forming a first electrode adapted to interact with second electrode means placed with respect to the applicator so as to be capacitively coupled thereto so that heating current supplied by the source of electromagnetic energy sufficient to elevate the temperature of tissue surrounding the applicator to a preselected temperature and for maintaining the preselected temperature during treatment will flow between the applicator and second electrode means during treatment;

positioning means for positioning and maintaining the positioning of the catheter means in the urethra so that the applicator means carried by the catheter means is and remains positioned adjacent the prostate tissue to be treated for as long as desired by the user; and temperature sensor supporting means attached to the catheter means for supporting a temperature sensing means in operative association with the applicator of the applicator means for measuring the temperature of the tissue surrounding the applicator.

2. An electromagnetic capacitive coupling applicator apparatus for treatment of benign prostatic hyperplasia comprising:

catheter means for insertion into the urethra including a fluid free tube, a temperature sensor supporting tube, and an applicator support portion adjacent to a first end of the fluid free tube;

applicator means including electrical conductor means mounted in the fluid free tube and an applicator connected to the electrical conductor means and mounted on the applicator support portion, said applicator forming a first electrode for applying electromagnetic energy into tissue adjacent to the applicator;

temperature sensor means including a temperature sensor inserted in the temperature sensor supporting tube for monitoring the temperature of tissue adjacent to the applicator;

electromagnetic energy generating means connected to the applicator means for supplying electromagnetic energy thereto;

second electrode means adapted to be positioned with respect to the applicator so as to be capacitively coupled thereto and connected to the electromagnetic energy generating means so that electromagnetic energy supplied by the electromagnetic energy generating means will flow between the applicator and the second electrode means to heat the tissue adjacent the applicator;

control means including a temperature reference means for setting a selected reference temperature to which the tissue is to be heated and a comparator connected to the temperature sensor means and temperature reference means for producing control signals; and said electromagnetic energy generating means being connected to the control means and responsive to the control signals for supplying electromagnetic energy to the applicator means sufficient for elevating the tissue temperature to the selected reference temperature and maintaining the tissue at the selected temperature during treatment.

3. An electromagnetic capacitive coupling applicator apparatus according to claim 2, wherein the applicator includes a helical coil type electrode.

4. An electromagnetic capacitive coupling applicator apparatus according to claim 2, wherein the applicator includes a plurality of flexible wires.

5. An electromagnetic capacitive coupling applicator apparator according to claim 2, wherein the applicator includes a flexible, electrically conductive sleeve.

6. An electromagnetic capacitive coupling applicator apparatus according to claim 2, wherein the applicator means includes an elongated coil having a length, and a sheath of dielectric material covering the elongated coil sufficiently for producing electromagnetic energy levels along the length of the coil to produce substantially uniform tissue temperature along the length of the coil.

7. An electromagnetic capacitive coupling applicator apparatus according to claim 2, wherein catheter means includes means for maintaining the position of the applicator means during treatment of the prostate.

8. An electromagnetic capacitive coupling applicator apparatus according to claim 7, wherein the means for maintaining the position of the applicator means during treatment includes a fluid drainage tube, an inflatable balloon mounted exteriorly thereof and adjacent to a first end of the fluid drainage tube, and a pressurized fluid source connected to the balloon whereby, when the first end of the fluid drainage tube is positioned within a bladder opening and the balloon inflated, the balloon engages the bladder opening for fixing the location of the applicator means.

9. An electromagnetic capacitive coupling applicator apparatus according to claim 2, wherein the applicator is mounted on the applicator support portion of the catheter means so as to be in direct electrical contact with the tissue to be heated when the catheter means is inserted in the urethra.

10. An electromagnetic capacitive coupling applicator apparatus according to claim 2, wherein the temperature sensor supporting tube is an elongate tube having a closed end portion adjacent the applicator means and mounted exteriorly of the fluid free tube.

11. A urethral inserted applicator for benign prostatic hyperplasia treatment by heating the prostate tissue surrounding the urethra using electromagnetic energy, comprising:

a multi-tube urinary catheter, said catheter having an insertion tip end for insertion into the urethra, a fluid dry tube closed at the insertion tip end, and an isolated open ended tube for urine drainage;

applicator means carried by the catheter, said applicator means including an applicator forming a first electrode adapted to interact with second electrode means placed with respect to the applicator so as to be capacitively coupled thereto so that heating current supplied by a source of electromagnetic energy will flow between the applicator and the second electrode means for heating tissue adjacent the applicator, and electrical conductor means enclosed by the fluid dry tube connected to the applicator and adapted to be connected to a source of electromagnetic energy; and dielectric insulation means covering the applicator for preventing direct contact of the applicator with adjacent tissue.

12. A urethral inserted applicator according to claim 11, wherein the multi-tube urinary catheter further includes a second fluid dry closed end tube, and an electromagnetic field compatible temperature sensor inserted in the second fluid dry closed tube for sensing the temperature of prostate tissue.

13. A urethral inserted applicator according to claim 11, wherein the applicator includes multiple electrode sections, each section adapted to be individually and selectively connected to a source of electromagnetic energy whereby the heating pattern length may be modified by controlling connection of the individual electrodes to the source of electromagnetic energy.

14. A urethral inserted applicator according to claim 11, wherein the applicator is a coil electrode and the coil has progressively increasing conductor width towards the insertion tip end of the catheter.

15. A urethral inserted applicator according to claim 11, wherein the applicator is a coil electrode and the coil has different turn ratios per unit length.

16. A urethral inserted applicator according to claim 11, wherein the thickness of the dielectric insulation means covering the applicator varies along the length of the applicator.

17. A urethral inserted applicator according to claim 11, wherein the applicator has a length and includes a plurality of individual coils along the length of the applicator, each coil adapted to be individually and selectively connected to a source of electromagnetic energy whereby the heating pattern length may be modified by controlling connections of the individual coils to the source of electromagnetic energy.

18. A system for controlling hyperthermia for benign prostatic hyperplasia comprising:

a flexible urethral catheter for insertion into the urethra, said catheter having an applicator means thereon for applying electromagnetic energy to tissues of a prostate gland surrounding the urethra to thereby cause heating of said tissues, and an electromagnetic field compatible temperature sensor for measuring the temperature of the heated tissues, said applicator means including an applicator forming a first electrode;

a second electrode;

an electromagnetic energy generating means for producing electromagnetic energy having a preselected frequency, said electromagnetic energy generating means being connected to the applicator and to the second electrode, said second electrode adapted to be positioned with respect to the applicator so as to be capacitively coupled thereto so that electromagnetic energy from the electromagnetic energy generating means will flow between the applicator and the second electrode; and a comparator means interconnecting the electromagnetic generating means and electromagnetic field compatible temperature sensor for comparing the measured temperature level to a preselected reference temperature level and to produce control signals for the electromagnetic energy generating means for controlling the supply of electromagnetic energy to the applicator means to control the tissue temperature.

19. A system for controlling hyperthermia for benign prostatic hyperplasia according to claim 18, wherein the second electrode is inserted into the rectum adjacent to the prostate gland and is a dielectrically insulated metallic cylinder with a diameter larger than the urethra inserted electrode.

20. A system for controlling hyperthermia for benign prostatic hyperplasia according to claim 18, wherein the second electrode is an electrically conductive material placed adjacent the skin tissue surface adjacent to the prostate tissue of a patient undergoing treatment.

* * * * *